(12) United States Patent
Söderholm et al.

(10) Patent No.: US 7,722,569 B2
(45) Date of Patent: May 25, 2010

(54) CATHETER ASSEMBLY WITH TIP SHIELD CLOSURE

(75) Inventors: Karl Johan Mårten Söderholm, Helsingborg (SE); Janne Joakim Lundqvist, Sjöbo (SE); Jörgen Bruno Hager, Helsingborg (SE); Lars-Åke Lennart Larsson, Lund (SE); Kristoffer Glowacki, Staffanstorp (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 393 days.

(21) Appl. No.: 11/439,479

(22) Filed: May 22, 2006

(65) Prior Publication Data

US 2007/0270754 A1 Nov. 22, 2007

(51) Int. Cl.
*A61M 5/178* (2006.01)
*A61M 5/00* (2006.01)
(52) U.S. Cl. .............. 604/164.08; 604/110; 604/164.01
(58) Field of Classification Search ................. 604/110, 604/164.08, 162, 164.07
See application file for complete search history.

(56) References Cited

U.S. PATENT DOCUMENTS

| | | | | |
|---|---|---|---|---|
| 5,348,544 A * | 9/1994 | Sweeney et al. | ............ | 604/192 |
| 5,697,907 A * | 12/1997 | Gaba | ........................ | 604/110 |
| 5,910,130 A * | 6/1999 | Caizza et al. | ................ | 604/110 |
| 6,234,999 B1 * | 5/2001 | Wemmert et al. | ........... | 604/162 |
| 6,527,747 B2 * | 3/2003 | Adams et al. | ............... | 604/162 |
| 6,749,588 B1 * | 6/2004 | Howell et al. | .......... | 604/164.08 |
| 6,855,130 B2 * | 2/2005 | Saulenas et al. | ............. | 604/110 |
| 2002/0177813 A1 * | 11/2002 | Adams et al. | .......... | 604/164.07 |
| 2005/0137528 A1 * | 6/2005 | Wilkinson | .................. | 604/110 |
| 2005/0251092 A1 * | 11/2005 | Howell et al. | ............. | 604/110 |
| 2007/0129689 A1 * | 6/2007 | Woehr et al. | ................. | 604/263 |
| 2007/0161950 A1 * | 7/2007 | Carlyon et al. | .............. | 604/110 |
| 2007/0270754 A1 * | 11/2007 | Soderholm et al. | ...... | 604/164.08 |

FOREIGN PATENT DOCUMENTS

| | | |
|---|---|---|
| EP | 1360970 A1 | 11/2003 |
| WO | WO 02/45786 | 6/2002 |
| WO | 2004043521 A1 | 5/2004 |
| WO | 2005053774 A1 | 6/2005 |

OTHER PUBLICATIONS

PCTUS2007012036-International Search Report.

* cited by examiner

*Primary Examiner*—Nicholas D Lucchesi
*Assistant Examiner*—Ian K Holloway
(74) *Attorney, Agent, or Firm*—Kinney & Lange, P.A.

(57) ABSTRACT

A tip shield of a catheter assembly has a resilient clip compartment, which may become blood-filled during use of the catheter assembly. The resilient clip inside the compartment is released upon withdrawal of the needle of the catheter assembly to disengage the catheter hub from the tip shield. The resilient clip also prevents re-exposure of the needle after being withdrawn into the tip shield. The blood-filled compartment may potentially leak or splash through an opening from the compartment when the resilient clip is released. A covering blocks the opening from the tip shield to minimize the risk of blood exposure. In addition, the covering minimizes the risk of premature release of the resilient clip and re-exposure of the needle.

20 Claims, 12 Drawing Sheets

CATHETER ASSEMBLY WITH TIP SHIELD CLOSURE

This application is related to an application entitled IV CATHETER ASSEMBLY WITH AN ERGONOMIC NEEDLE GRIP, which was filed on the same day and also assigned to Becton, Dickinson and Company.

BACKGROUND OF THE INVENTION

The present invention relates to a catheter assembly. In particular, the present invention relates to a tip shield for a catheter assembly.

Intravascular catheters are used for infusing fluid into a patient, withdrawing fluid from a patient, or monitoring various parameters of the patient's vascular system. Typically, a needle is used to introduce the catheter into a patient's blood vessel. A catheter is mounted over a needle that has a sharp distal tip with at least the distal portion of the catheter tightly engaging the outer surface of the needle to prevent peel-back of the catheter during insertion into the blood vessel.

A clinician inserts the catheter and needle through the patient's skin and into the patient's blood vessel. Once a flashback of blood is seen within a flashback chamber, the catheter is threaded over the needle and inserted completely into the blood vessel. The needle is then withdrawn from the catheter leaving the catheter in place. Once the needle is withdrawn from the catheter, the needle is a "blood-contaminated sharp" and must be properly handled.

In recent years, there has been great concern over accidental needle sticks by blood-contaminated sharps. Although aware of the need to properly handle blood-contaminated sharps, accidental needle sticks with contaminated needles still occur, for example, during emergency situations or as a result of inattention or neglect. As a result of this problem, various needle shields have been developed. Besides protecting clinicians from accidental needle sticks, needle shields should also minimize exposure to blood during and after the catheter insertion process.

BRIEF SUMMARY OF THE INVENTION

The present invention reduces the risk of leakage or splash of blood from the tip shield of a catheter assembly. The tip shield includes a resilient clip compartment, which may become filled with blood during use. The blood may leak or splash out of an opening on the downside of the compartment. The covering of the present invention blocks the opening to prevent leakage and splash from the compartment.

DETAILED DESCRIPTION

Figure 1:
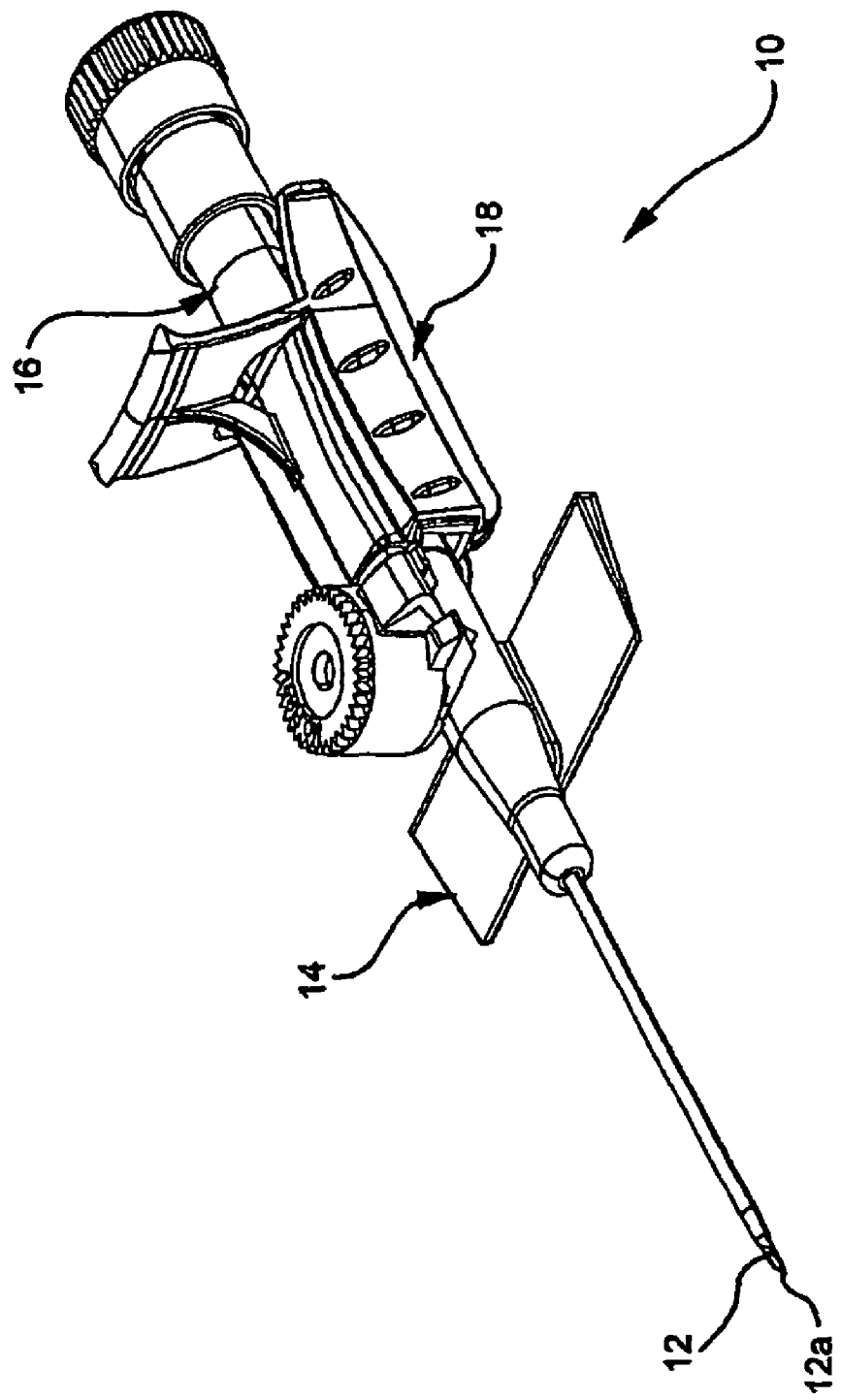
FIG. 1 is a perspective view of a representative embodiment of a catheter assembly prior to insertion.

FIG. 1 is a representative embodiment of catheter assembly 10 prior to placement in a vessel. Catheter assembly 10 includes needle 12 with needle tip 12a, catheter hub 14 and needle hub 16 with grip portion 18. The distal end of catheter assembly 10 is generally toward needle tip 12a and the proximal end is generally toward needle hub 16. Lateral regions are situated at or extending toward the sides of catheter assembly 10. Medial regions are at or toward the midline of catheter assembly 10, with the midline running in a longitudinal direction.

Figure 2:
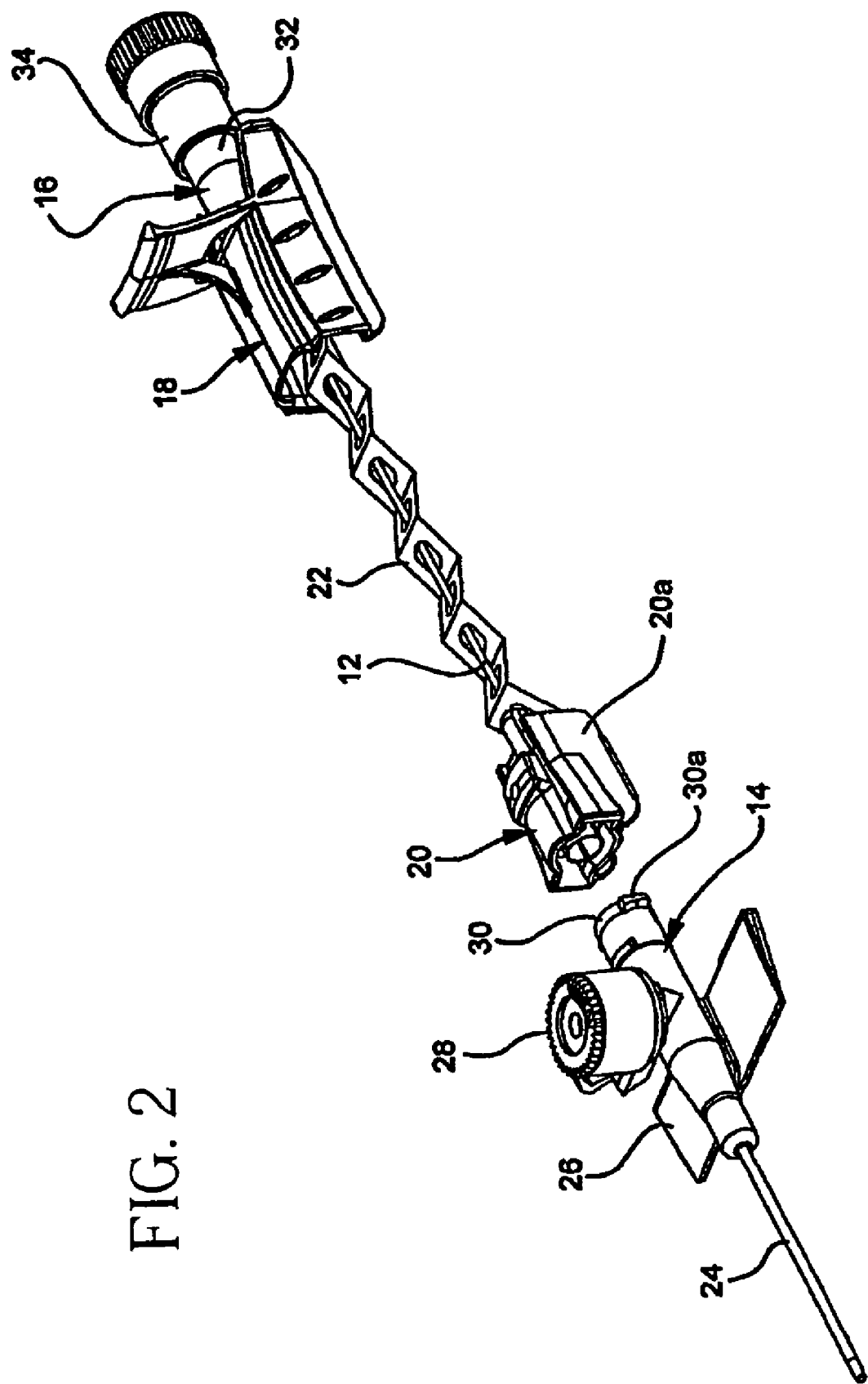
FIG. 2 is a perspective view of a representative embodiment of a catheter assembly after insertion.

FIG. 2 shows catheter assembly 10 after placement into a vessel. In addition to the elements shown in FIG. 1, FIG. 2 includes tip shield 20 with housing 20a and tether 22. Catheter hub 14 includes catheter 24, wings 26, injection port 28 and notch 30 with luer lock member 30a. Needle hub 16 includes flashback chamber 32 and flow control plug 34.

In use, needle 12 of the assembled catheter assembly 10 shown in FIG. 1 is inserted at an angle through the patient's skin into a blood vessel. Placement of needle 12 with catheter 24 in a blood vessel is verified by confirming that there is a flashback of blood in flashback chamber 32. Once confirmed, pressure is applied to the blood vessel distal of needle 12 by pressing down on the patient's skin. This pressure occludes or at least minimizes further blood flow through needle 12 and catheter 24. Needle 12 is then withdrawn from catheter 24 by pulling needle hub 16 in a proximal direction from catheter hub 14 leaving catheter 24 in place in the patient's blood vessel.

As needle 12 is withdrawn from catheter 24, needle hub 16 pulls away in a proximal direction from tip shield 20. As this occurs, tether 22 unfolds to extend between needle shield 20 and grip portion 18. When needle tip 12a is withdrawn into tip shield 20, tip shield 20 disengages from catheter hub 14. At this point, tip shield 20 now covers needle tip 12a to prevent accidental needle sticks. The length of tether 22 is such that when fully extended, tip shield 20 encompasses needle tip 12a. Tether 22 prevents tip shield 20 from falling off needle tip 12a. The clinician is then able to discard needle 12.

Figure 3:
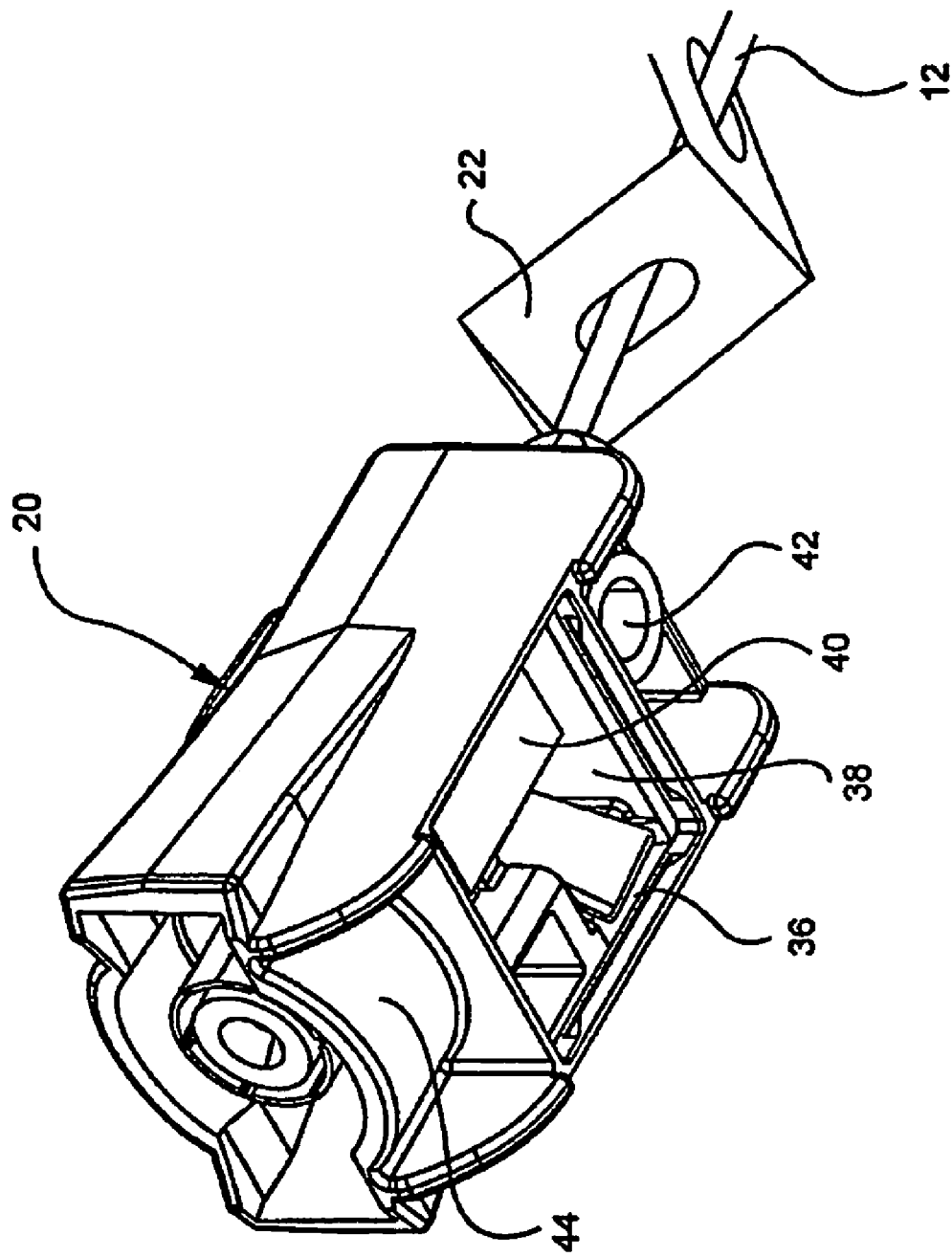
FIG. 3 is a perspective view of a representative embodiment of a tip shield.

FIG. 3 shows a detailed view of a representative embodiment of tip shield 20. Opening 36 is on the underside of tip shield 20 and opens up into resilient clip compartment 38. Resilient clip 40 is positioned within compartment 38. Tether attachment post 42 is positioned on the proximal end of tip shield 20 and attaches tether 22 to tip shield 20. Connector 44 is at the distal end of needle shield 20 and connects catheter hub 14 and tip shield 20. As shown in FIG. 3, needle tip 12a is shielded within tip shield 20, which is now separated from catheter hub 14. The mechanism which disengages tip shield 20 from catheter hub 14 once needle 12 has been withdrawn, is resilient clip 40.

Figure 4:
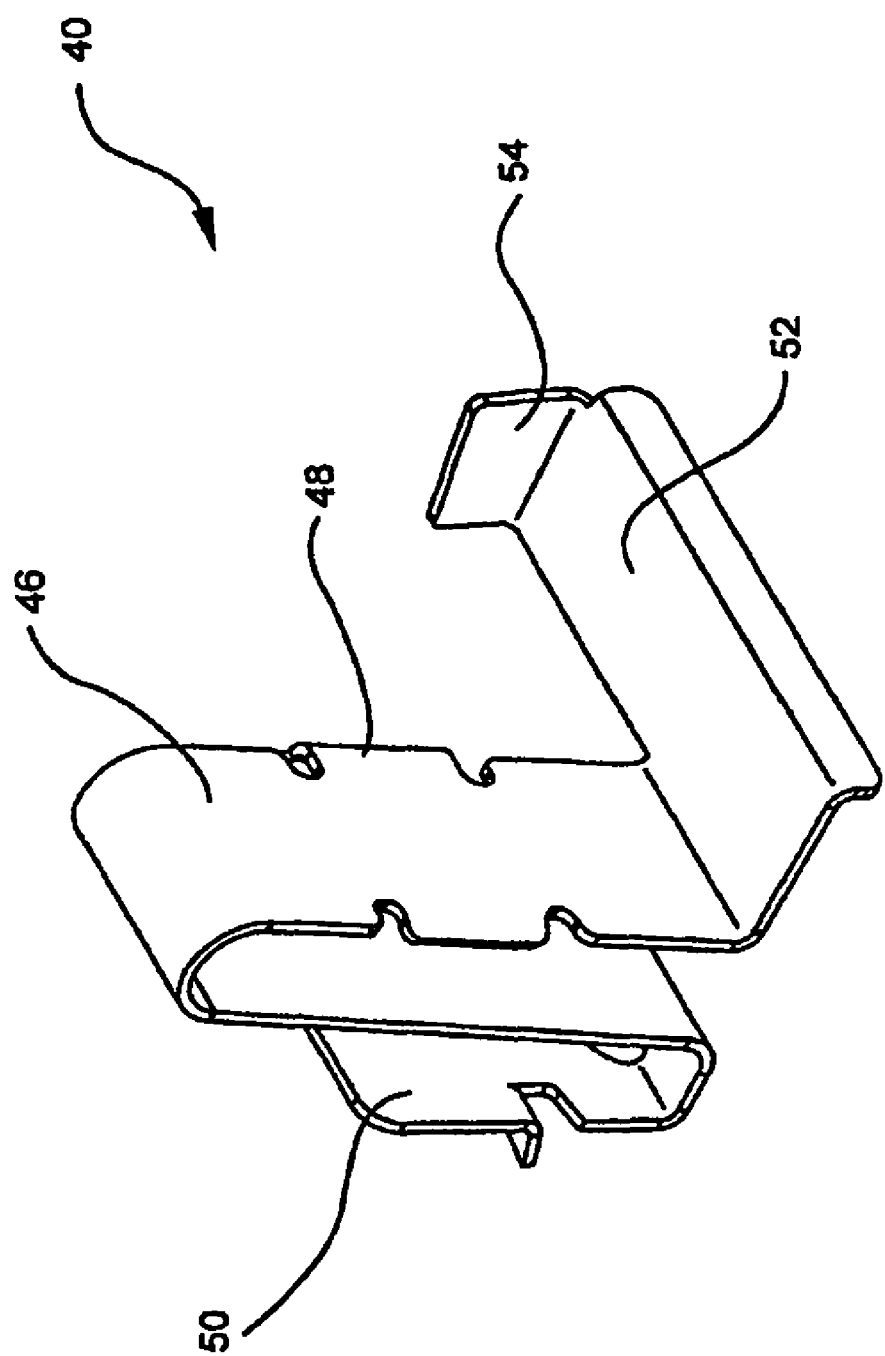
FIG. 4 is a perspective view of a representative embodiment of a resilient clip.
Figure 5:
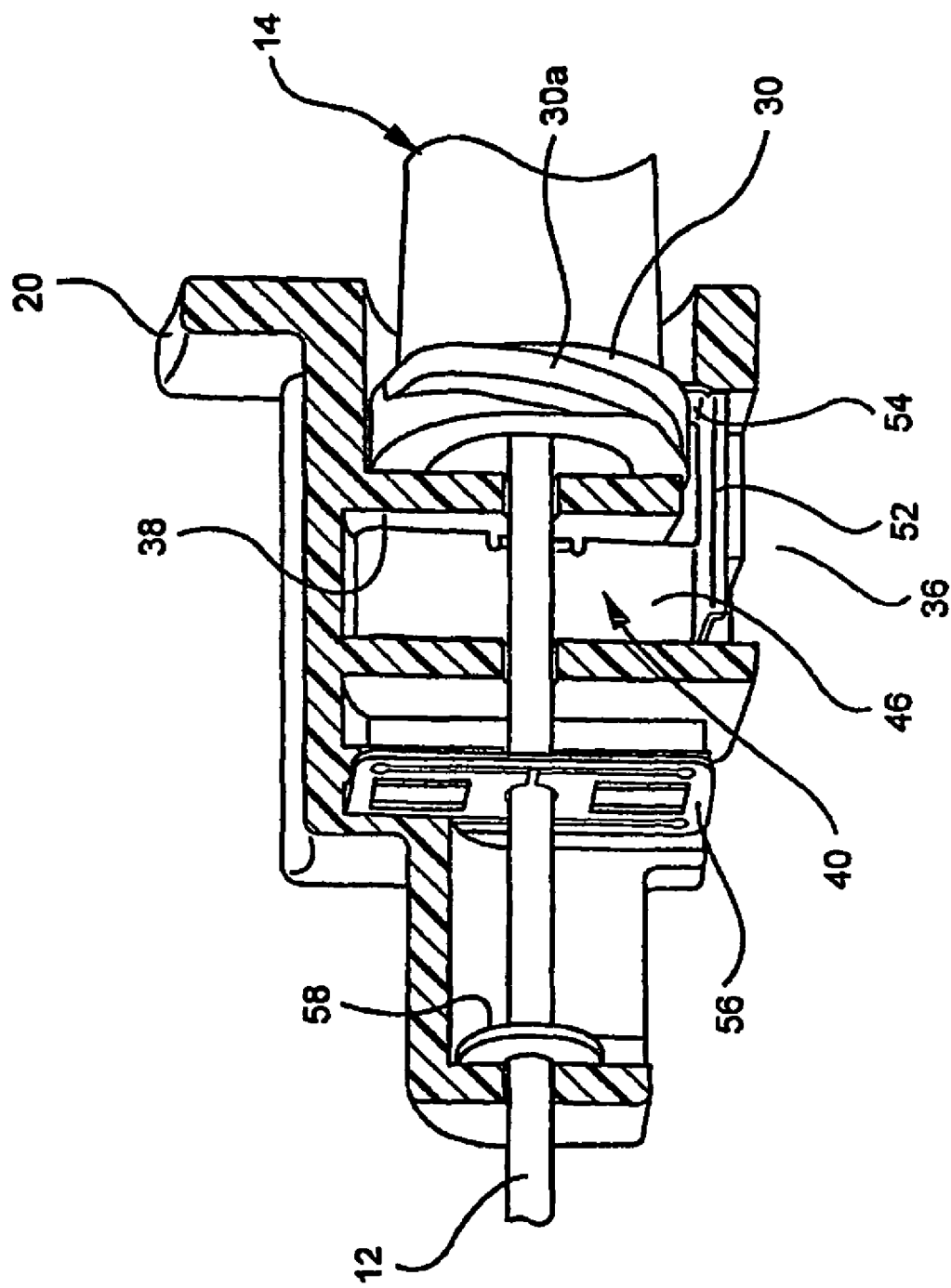
FIG. 5 is a partial cross-sectional view of a representative embodiment of a resilient clip compartment prior to insertion.
Figure 6:
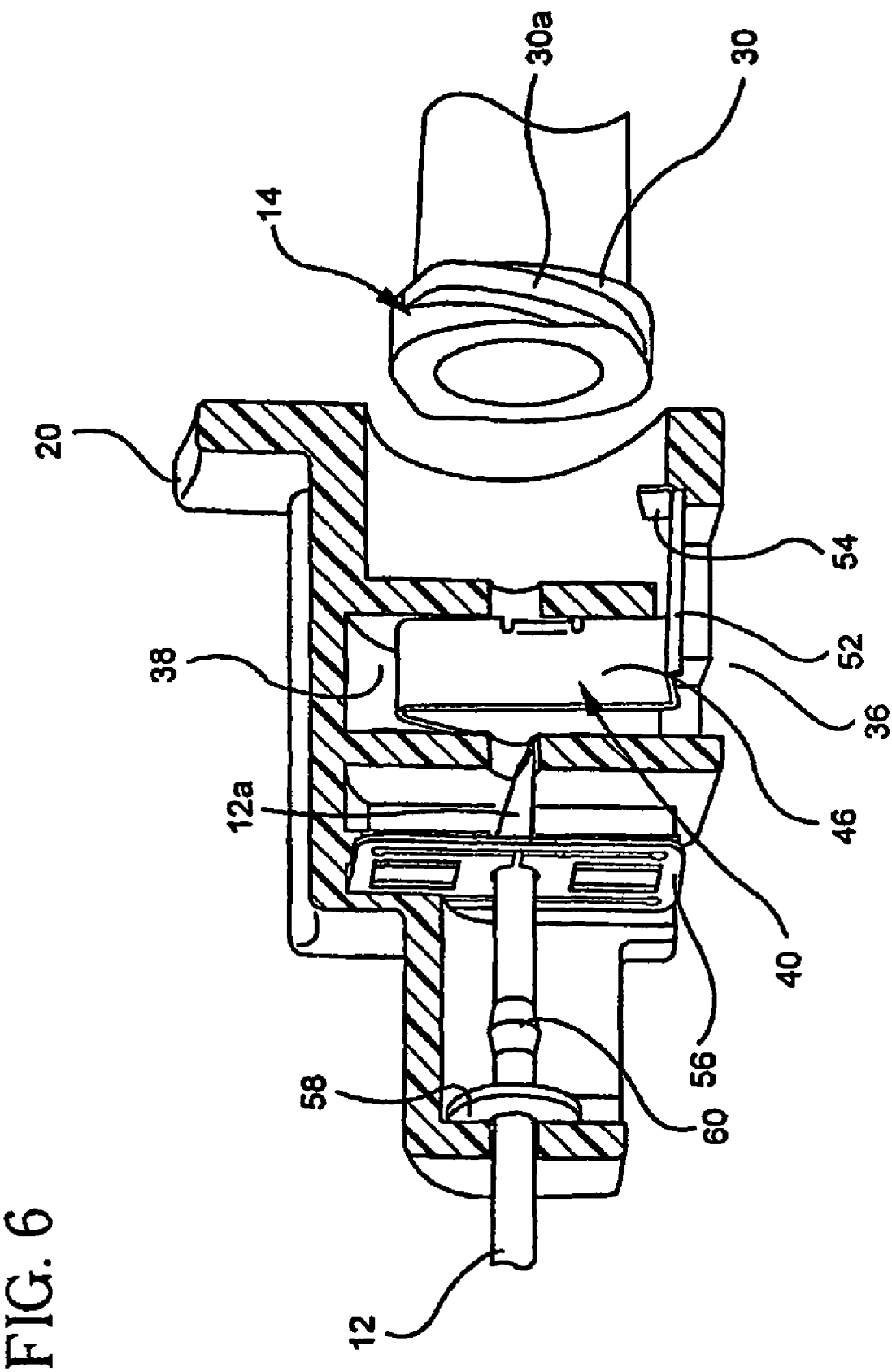
FIG. 6 is a partial cross-sectional view of a representative embodiment of a resilient clip compartment after insertion.

FIG. 4 shows a representative embodiment of resilient clip 40. Resilient clip 40 includes spring clip 46, block 48, tab 50, arm 52 and finger 54. Resilient clip 40 is positioned within compartment 38 and attaches to a lateral wall within compartment 38 via tab 50. Resilient clip 40 is further positioned such that arm 52 extends distally from spring clip 46 to attach to catheter hub 14 via finger 54. FIGS. 5 and 6 illustrate resilient clip 40 in use. Note that the views shown in FIGS. 5 and 6, as well as other subsequent figures, are reversed from previous figures such that "distal" is to the right and "proximal" is to the left.

FIGS. 5 and 6 are cross-sectional views of an alternate version of tip shield 20 that may also be used with the present invention. Instead of tether 22, this alternate embodiment of tip shield 20 utilizes a different mechanism, discussed below, to limit the distance needle tip 12a can move proximally within tip shield 20.

FIG. 5 shows tip shield 20 prior to withdrawal of needle 12. In addition to tip shield 20, FIG. 5 also shows a portion of catheter hub 14 with notch 30 and an alternative embodiment of needle 12. FIG. 5 also shows retention plate 56 and washer 58 within the alternative embodiment of tip shield 20.

In either embodiment, when catheter assembly 10 is assembled prior to use, needle 12 compresses spring clip 46 within tip shield 20. When spring clip 46 is compressed, arm 52 is held in a medial, biased position, which in turn positions finger 54 to engage notch 30 of catheter hub 14 and connects tip shield 20 with catheter hub 14. Notch 30 may also take the form of a slot or indent, or finger 54 may instead engage luer lock member 30a. In the example shown, luer lock member 30a is a thread. With the configuration shown in FIG. 5, tip shield 20 and catheter hub 14 are securely connected.

Upon withdrawal of needle 12 after insertion of catheter 24 into a patient's vessel, needle tip 12a is moved proximally into tip shield 20 as is illustrated in FIG. 6. Enlarged diameter portion 60 of the alternative embodiment of needle 12 has a slightly larger diameter than the rest of needle 12. Washer 58 has an inside diameter that is slightly larger than most of needle 12 except for enlarged diameter portion 60. As needle 12 moves proximally, enlarged diameter portion 60 of needle 12 eventually encounters washer 58, which prevents any further proximal movement of needle 12 relative to tip shield 20. The distance between enlarged diameter portion 60 and needle tip 12a of needle 12 is such that needle tip 12a is now on the proximal side of resilient clip 40. With needle 12 no longer compressing spring clip 46, arm 52 moves to a generally lateral, unbiased position. This movement by arm 52, in turn, moves finger 54 such that it disengages from notch 30. The disengagement of finger 54 from notch 30 effectively disconnects catheter hub 14 from tip shield 20 allowing catheter hub 14 to remain with the patient. Needle tip 12a is shielded within tip shield 20, and notably, block 48, which is a tab extending from spring clip 46, prevents needle 12 from moving distally back through tip shield 20 once spring clip 46 is released and no longer compressed by needle 12.

As described above, tip shield 20 effectively shields clinicians from accidental needle sticks. Another function of tip shield 20 is minimization of exposure to patient blood. When needle 12 is withdrawn after insertion into the patient's vessel, blood may remain on or around needle tip 12a and be drawn into compartment 38 of tip shield 20. The release of resilient clip 40 as needle tip 12a moves past resilient clip 40 (FIG. 6) may cause this blood to splash. Blood may leak or splash out of tip shield 20 via opening 36 leading to exposure. Blocking opening 36 with a means for blocking will minimize the risk of exposure by containing blood within tip shield 20. Examples of various means for blocking opening 36 are described below.

Figure 7:
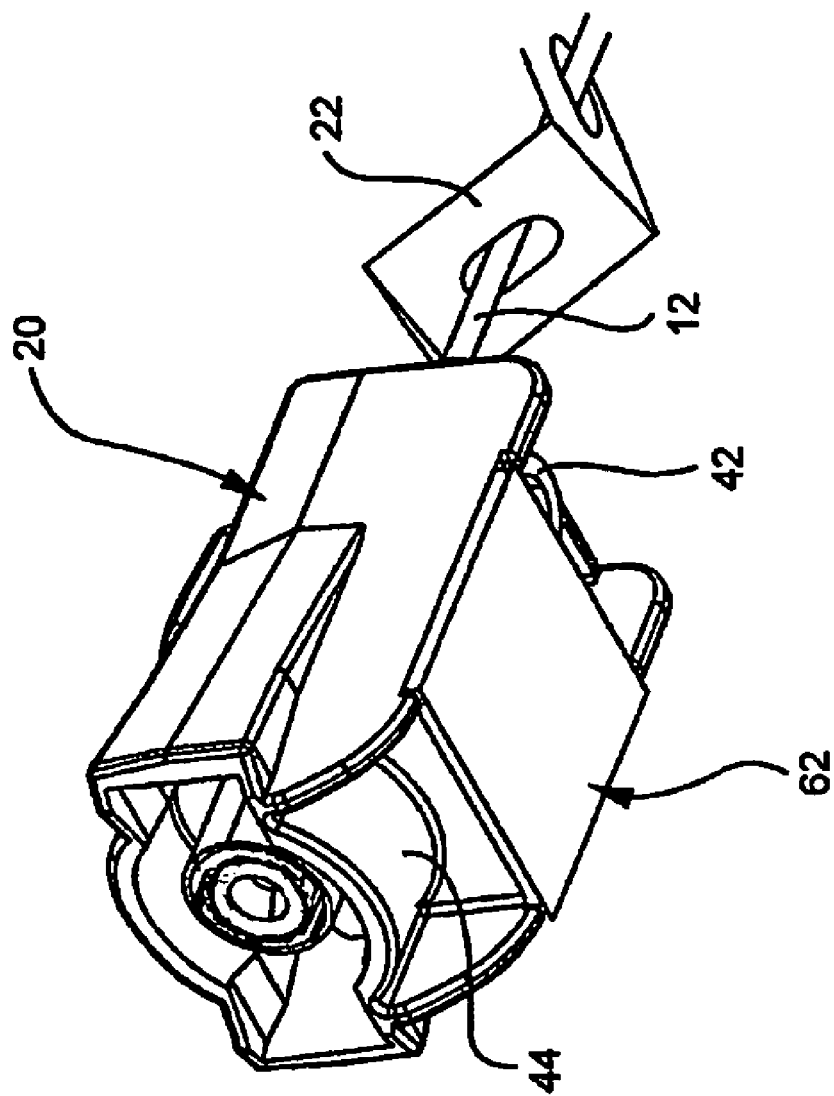
FIG. 7 is a perspective view of a first representative embodiment of a tip shield closure.

FIG. 7 is a representative embodiment of a covering to block opening 36. Lid 62 is sized to cover opening 36 and can be fabricated from any of a number of various materials. Some materials are, for example, relatively stiff plastics or metals. These materials may be attached by chemical and/or mechanical means such as by adhesive; heat, ultrasonic or friction heat welding; melting, snaps, etc.

Figure 8B:
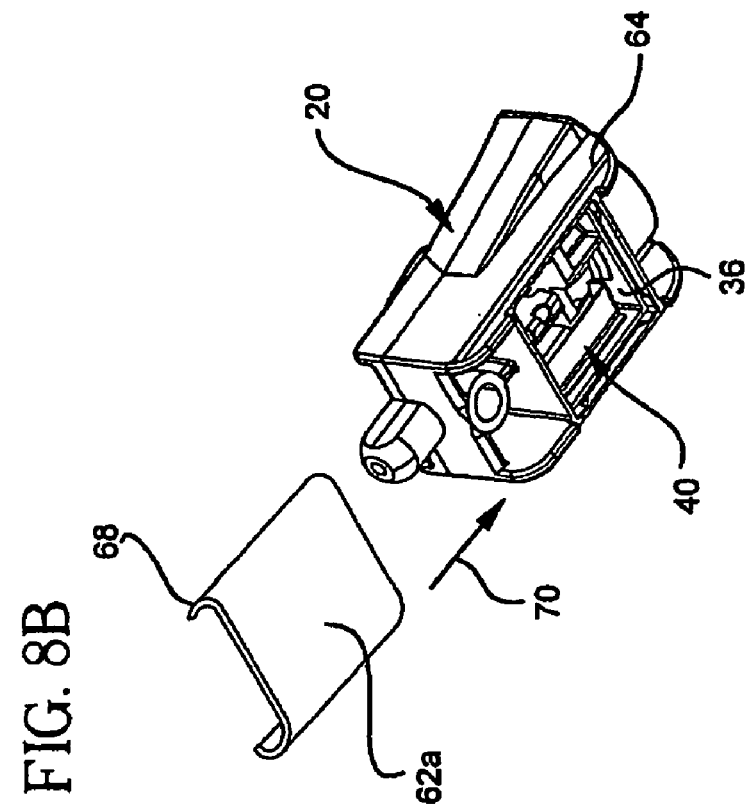
FIG. 8B is a perspective view of a second representative embodiment of attaching a tip shield closure.
Figure 8A:
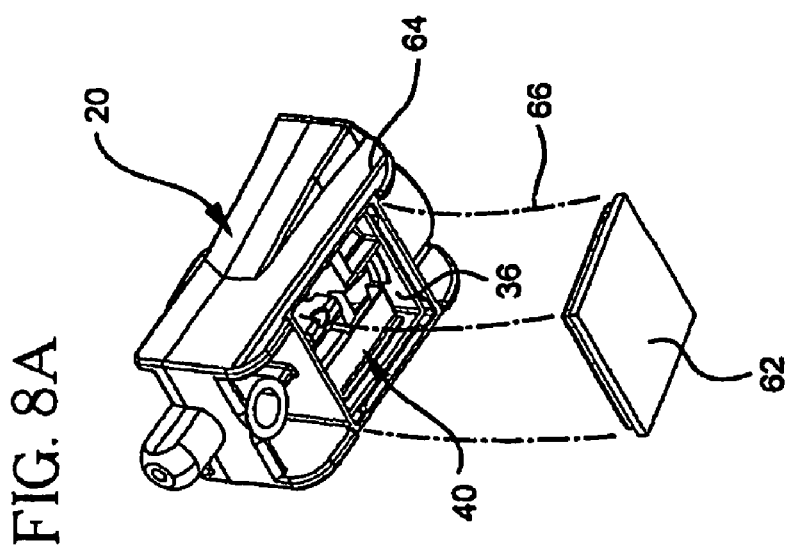
FIG. 8A is a perspective view of a first representative embodiment of a attaching a tip shield closure.

Two representative embodiments of attaching a covering such as lid 62 is shown in FIGS. 8A and 8B. FIG. 8A shows lid 62 and arrows 66. Lid 62 is a simple covering that is placed over opening 36 as indicated by arrows 66. Attachment to tip shield 20 is via any of the chemical and/or mechanical methods described above.

FIG. 8B includes ridge 64 along opening 36 of tip shield 20 and lid 62a with lips 68 and arrows 70. Lid 62a is slidably mounted over opening 36 as indicated by arrows 70 and may be mounted from the proximal end of tip shield 20 as shown or from the distal end of tip shield 20. Lips 68 of lid 62a engage ridges 64 of tip shield 20 (a second ridge 64 along the opposing edge of opening 36 is not shown) and slide over opening 36. Typically, lid 62a is also attached to needle shield 20 via any of the previously described chemical and/or mechanical methods.

Lid 62 shown in FIG. 7 may also be fabricated from relatively flexible materials such as adhesive tape or film. The adhesive tape simply adheres to at least one of the edges of opening 36 and may also extend beyond one or more edges to adhere to housing 20a of tip shield 20 for stronger attachment. Alternatively, the adhesive tape of lid 62 may extend all the way around tip shield 20, similar to a sleeve, and attach to itself.

A film may be attached with adhesive or any of the previously described methods. Again, the film may be attached to at least one of the edges around opening 36 and may also extend beyond one or more of the edges to attach to housing 20a of tip shield 20 and/or itself.

Figure 9B:
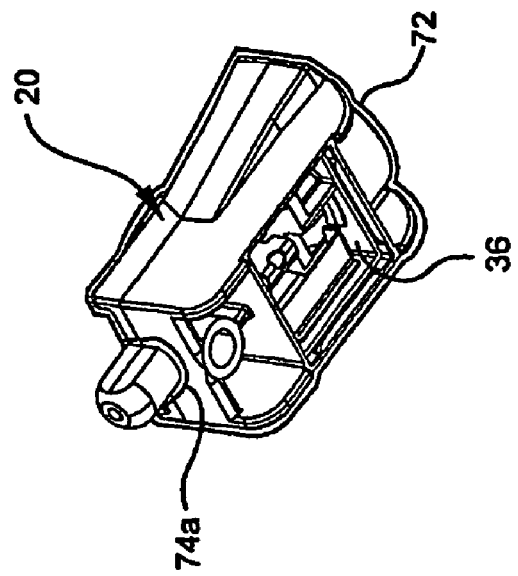
FIGS. 9A and 9B are perspective views of a third representative embodiment of a tip shield closure.
Figure 9A:
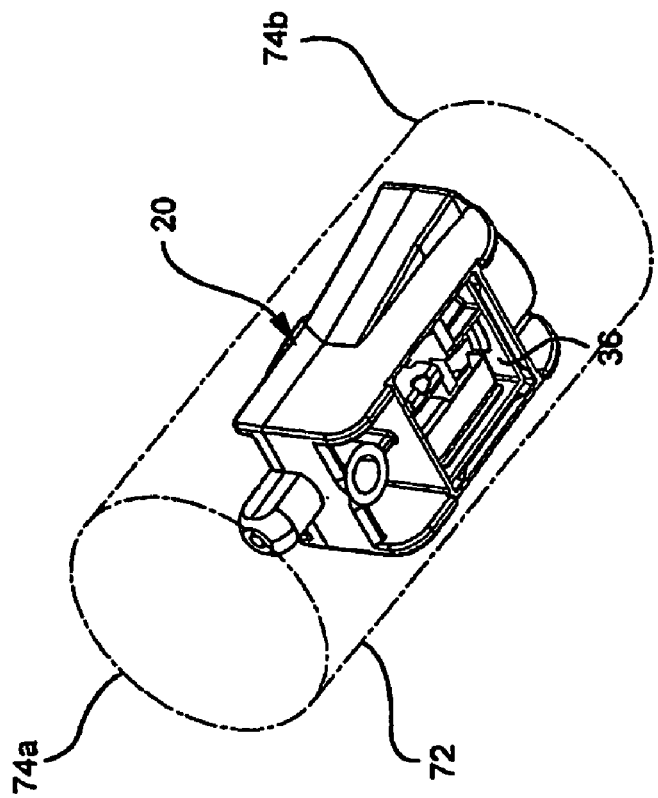

FIGS. 9A and 9B illustrate another representative embodiment for covering opening 36. FIG. 9A shows sleeve 72 loosely encompassing tip shield 20. Sleeve openings 74a and 74b are positioned at the proximal and distal ends of tip shield 20, respectively. When heat is applied to sleeve 72, typically blown hot air, sleeve 72 shrinks and conforms to the shape of tip shield 20. In a variation of this embodiment, sleeve 72 may be a plastic sleeve that is not shrink-wrap material. Sleeve 72 is sized to fit tight enough around tip shield 20 to prevent leakage or splash from compartment 38.

FIG. 9B shows sleeve 72 after shrinkage around tip shield 20. Sleeve 72 conforms to the shape of tip shield 20 and is shown as a layer covering the outer surface of tip shield 20. Opening 36 is now sealed to minimize any leakage or splash of blood from tip shield 20, while openings 74a and 74b allow access to the proximal and distal ends.

Figure 10:
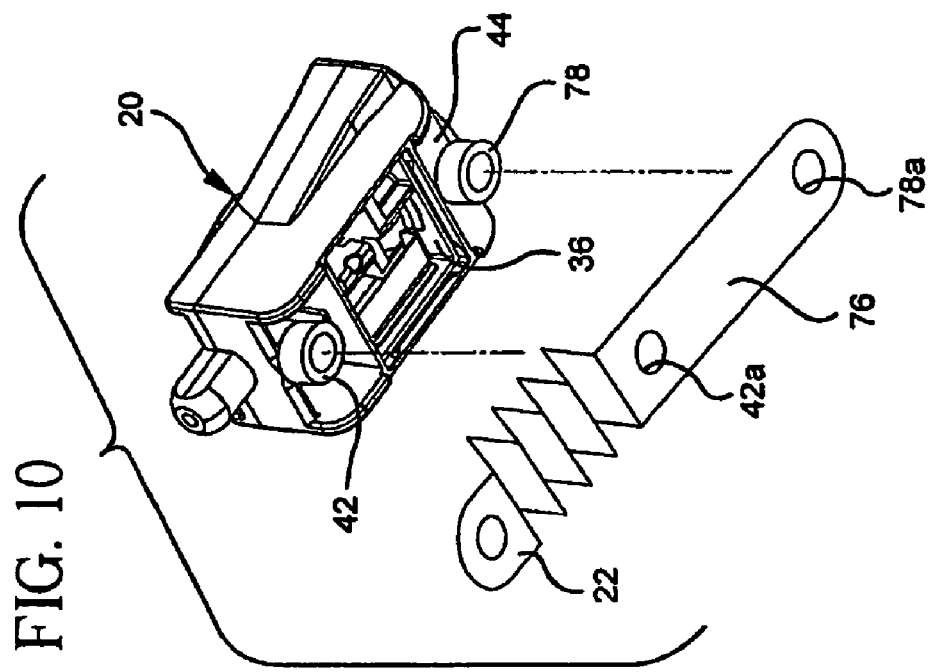
FIG. 10 is a perspective view of a fourth representative embodiment of a tip shield closure.

Alternatively, a covering may be derived as an extension of one of the components of catheter assembly 10. FIG. 10 is a representative embodiment of an extension of tether 22. Tether 22 is extended to form lid 76, which includes holes 42a and 78a. Tip shield 20 includes an additional tether attachment post 78 on connector 44. Lid 76 is attached to tip shield 20 by inserting posts 42 and 78 through holes 42a and 78a, respectively. Lid 76 may otherwise be secured to tip shield 20 by any of the previously discussed methods, if desired, without the addition of post 78 and hole 78a. Alternatively, the previously discussed adhesive, welding or melting methods can be used in addition to attachment via post 78 and hole 78a to further seal or block opening 36.

Figure 11:
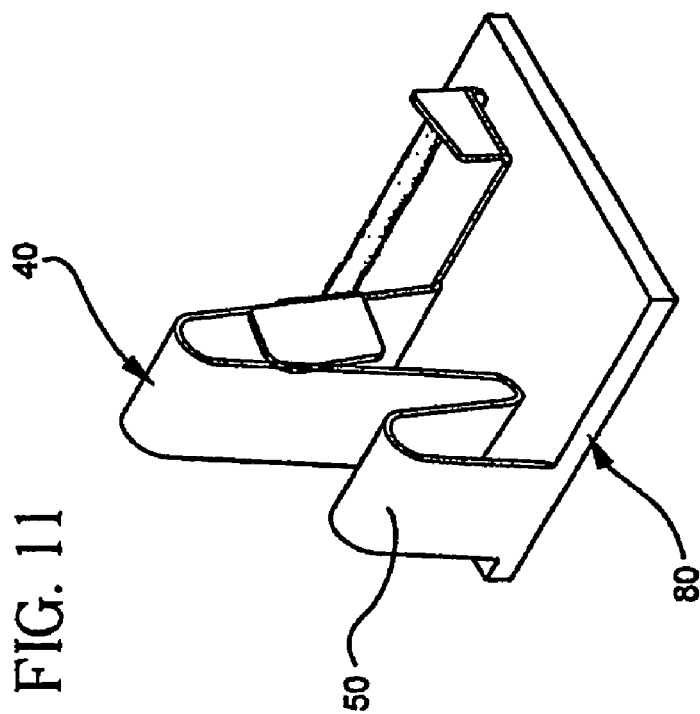
FIG. 11 is a perspective view of a fifth representative embodiment of a tip shield closure.

FIG. 11 is a representative embodiment showing an extension of resilient clip 40. In this embodiment, lid 80 is formed as an extension of tab 50 of resilient clip 40. Lid 80 is typically fabricated from the same metallic material used to fabricate resilient clip 40. Again, lid 80 is sized to block opening 36 of tip shield 20 and may be attached by any of the chemical and/or mechanical methods described above.

Figure 12:
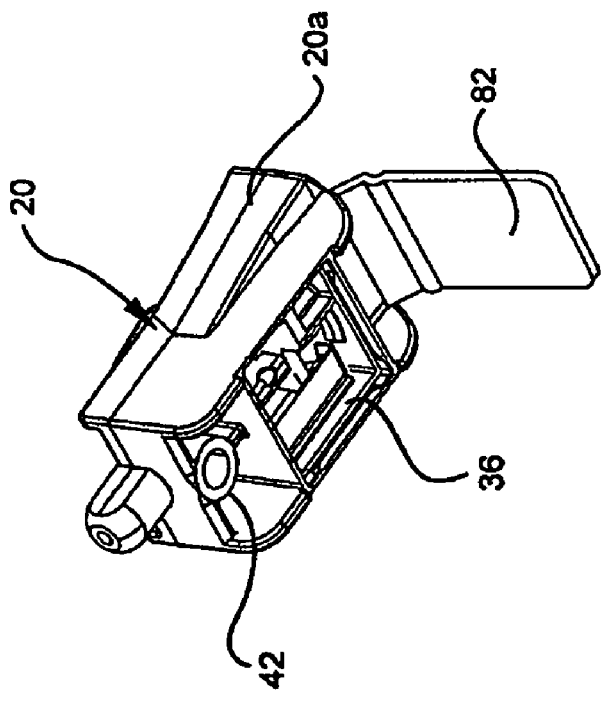
FIG. 12 is a perspective view of a sixth representative embodiment of a tip shield closure.

FIG. 12 is a representative embodiment of an extension of housing 20a. Lid 82 is formed as an integral part of housing 20a. Typically, lid 82 is bent or folded at the point where lid 82 meets housing 20a, but a hinge may also be used to connect lid 82 and housing 20a. Though lid 82 is shown attached to housing 20a at the distal end of tip shield 20, it may instead be attached at the proximal end or either lateral side of tip shield 20. Once the components, including resilient clip 40, are assembled within compartment 38, lid 82 is attached using one of the chemical and/or mechanical methods described above.

Figure 13:
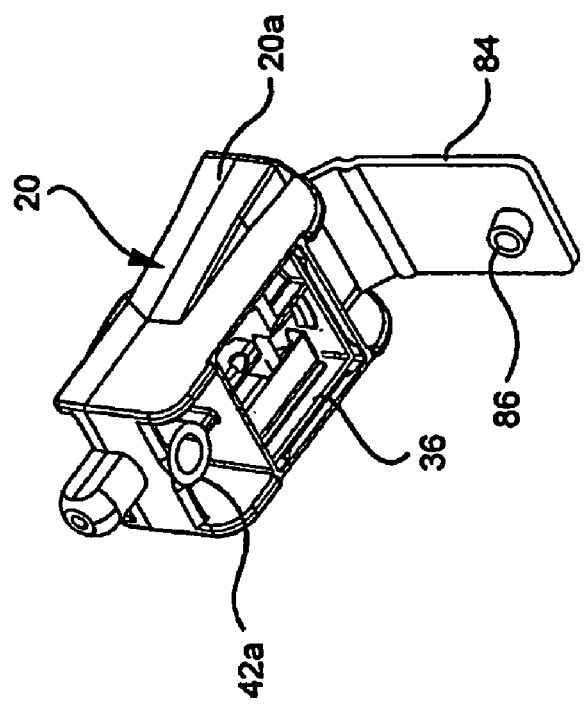
FIG. 13 is a perspective view of a seventh representative embodiment of a tip shield closure.

FIG. 13 is another representative embodiment of an extension of housing 20a. In this embodiment, tip shield 20 includes tether attachment post 42a and lid 84 with lid attachment knob 86. Post 42a functions as an attachment for tether 22 as well as a means for attachment of lid 84. Post 42a is a cylindrical tube, and its inside diameter is sized to mate with knob 86 such that knob 86 is secured within post 42a by frictional force. Post 42a and knob 86 can mate using any shape besides the circular shape shown. The mating of post 42a and knob 86, in turn, secures lid 84 over opening 36, while at the same time preventing tether 22 from slipping off post 42a. Attachment may be further secured use one of the chemical and/or mechanical methods described above. For example, post 42a and knob 86 may be coupled with a snap or adhesive or both. Alternatively, adhesive or welding may be used as a seal along the interface between the edges of opening 36 and lid 84.

In another representative embodiment of a covering for blocking opening 36, compartment 38 is filled with a high viscosity fluid such as grease or a similar-type product that minimizes leakage or splash from compartment 38. Petroleum jelly is an example of one such product. Typically, compartment 38 would be filled with the product after the components are assembled within compartment 38. This embodiment may also be combined with any of the previously described embodiments.

Figure 14:
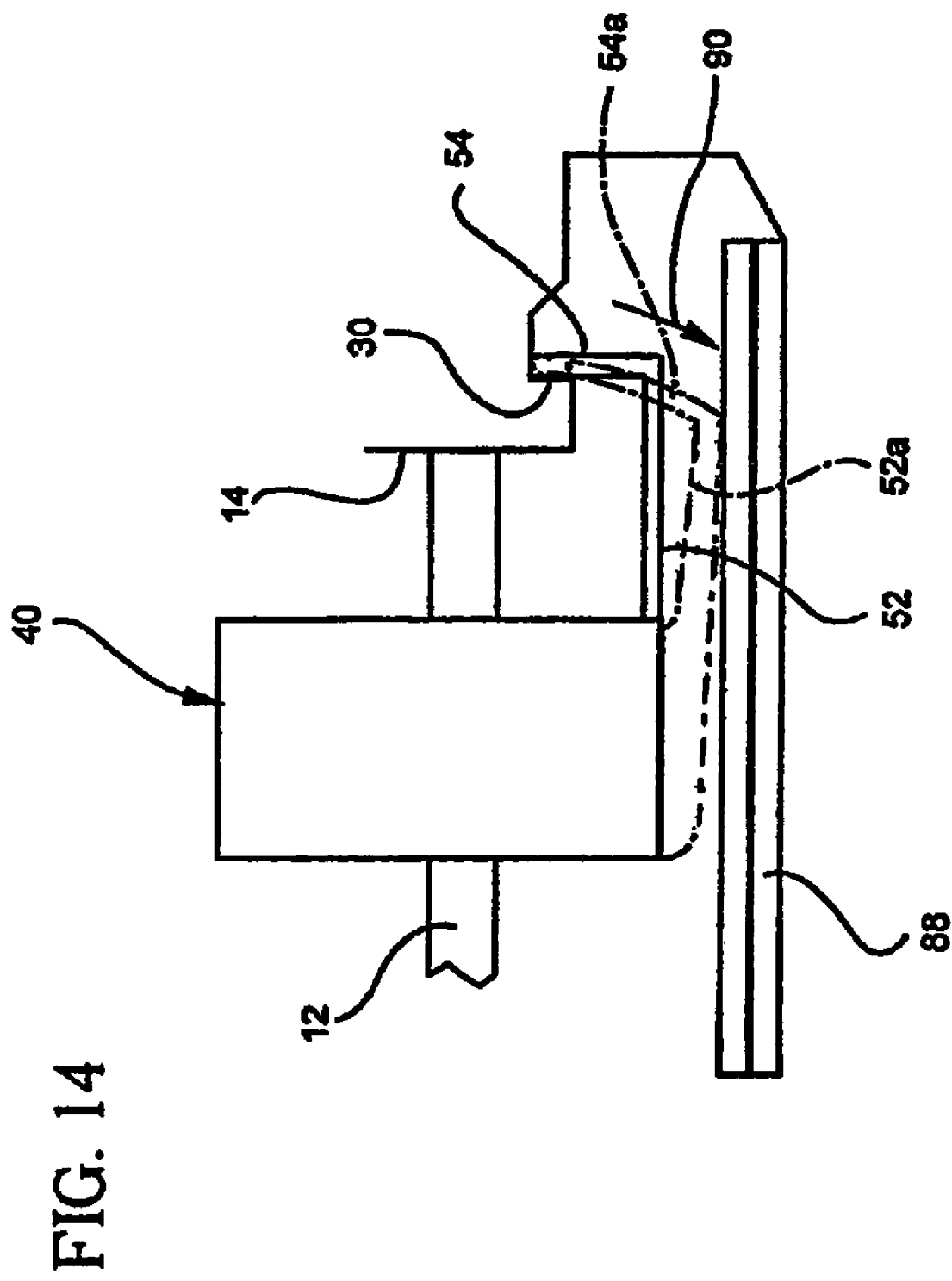
FIG. 14 is a partial cross-sectional view of a representative embodiment of a resilient clip compartment and tip shield closure.

Besides minimizing leakage or splash from compartment 38, a covering over opening 36 provides the added benefit of minimizing the risk of premature detachment of catheter hub 14 from tip shield 20. FIG. 14 illustrates this concept. FIG. 14 shows resilient clip 40 in its medial, biased position prior to withdrawal of needle 12. Lid 88 represents any of the previously described coverings that block opening 36. Arm 52 with finger 54 extends from spring clip 46 and finger 54 engages notch 30 as described previously. In addition, arm 52a with finger 54a is shown in phantom.

In use, under certain circumstances, mishandling of catheter assembly 10 may result in premature release of finger 54 from notch 30 before needle tip 12a is withdrawn into tip shield 20 to release resilient spring 40. Arrow 90 represents the motion of finger 54 during premature release. Covering 88 stops arm 52 and finger 54 at a position represented by arm 52a and finger 54a. At this position, finger 54a is still engaged with notch 30 thereby preventing release of catheter hub 14.

Along the same lines, covering 88 can minimize the possibility of re-exposing needle tip 12a after proper release of resilient clip 40. As described above (FIG. 4), resilient clip 40 includes block 48, which is a tab that prevents needle 12 from being pushed back through tip shield 20 once resilient clip 40 is properly released. If resilient clip 40 releases in a manner where block 48 is not aligned properly with needle 12 to block proximal movement of needle 12 out of tip shield 20, needle tip 12a could be pushed proximally back through and out of tip shield 20. Covering 88 minimizes this possibility by confining resilient clip 40 and limiting movement or slippage downward and out of compartment 38. Thus, needle tip 12a and block 48 are less likely to be misaligned.

In addition, covering 88 minimizes the possibility of reactivating catheter assembly 10 by tampering with resilient clip 40 after use. In most of the embodiments shown, covering 88 is attached permanently over opening 36 making difficult to access compartment 38.

A covering according to the present invention for blocking opening 36 of compartment 38 minimizes the risk of exposure to contaminated blood, premature release of tip shield 20 from catheter hub 14 and re-exposure of needle tip 12a subsequent to proper release of resilient clip 40. These benefits provide a safer experience during insertion of an IV catheter for the clinician as well as the patient.

Although the present invention has been described with reference to preferred embodiments, workers skilled in the art will recognize that changes may be made in form and detail without departing from the spirit and scope of the invention.

The invention claimed is:

1. A catheter assembly comprising:
   a catheter hub;
   a needle hub;
   a needle attached to the needle hub and inserted through the catheter hub;
   a tip shield having a distal end connectable to the catheter hub, a proximal end connectable to the needle hub, a first sidewall located between the distal end and the proximal end, and an opening in the first sidewall to permit access to a resilient clip compartment during assembly, the tip shield being connectable to the needle hub;
   a resilient clip insertable into the resilient clip compartment through the opening in the first sidewall, the resilient clip including a U-shaped spring clip, a tab attached to a first end of the U-shaped spring clip, and a distally extending arm attached to a second end of the U-shaped spring clip, the U-shaped spring clip being laterally compressed between the needle and the tab attached to a second sidewall of the resilient clip compartment when the needle is inserted through the catheter hub, and the U-shaped spring clip moving laterally away from the tab when the needle is removed from the catheter hub, the distally extending arm being attached to the catheter hub when the U-shaped spring clip is laterally compressed between the needle and the tab, and the distally extending arm releasing its attachment to the catheter hub when the needle is removed from the catheter hub; and
   a covering blocking the opening in the first sidewall of the resilient clip compartment to minimize fluid leakage from the tip shield upon release of the distally extending arm of the resilient clip from the catheter hub.

2. The catheter assembly of claim 1 wherein a position of the covering minimizes risk of premature release of the resilient clip from the catheter hub.

3. The catheter assembly of claim 1 wherein a position of the covering minimizes risk of re-exposure of the needle after release of the resilient clip from the catheter hub.

4. The catheter assembly of claim 1 wherein the covering is attached to the tip shield by at least one of chemical attachment and mechanical attachment.

5. The catheter assembly of claim 1 wherein the covering is a lid.

6. The catheter assembly of claim 1 wherein the covering is a film.

7. The catheter assembly of claim 1 wherein the covering is a high viscosity fluid.

8. The catheter assembly of claim 1 wherein the covering is an extension of the resilient clip.

9. The catheter assembly of claim 1 further comprising:
a tether connecting the tip shield and the needle hub;
wherein the covering is an extension of the tether.

10. A tip shield for use in a catheter assembly having a needle, a catheter hub, a needle hub, and distal and proximal ends, the tip shield comprising:
a housing having a distal end connectable to the catheter hub, a proximal end connectable to the needle hub, and an opening in a sidewall located between the distal and proximal ends;
a resilient clip insertable through the opening into the housing, the resilient clip having a U-shaped spring clip, a tab attached to a first end of the U-shaped spring clip, and a distally extending arm attached to a second end of the U-shaped spring clip, the spring clip being movable toward the tab into a laterally compressed position where the arm is held in a medial, biased position for engagement with the catheter hub, and the spring clip being movable away from the tab into a laterally extended position where the arm is moved to a lateral, unbiased position for disengagement from the catheter hub; and
means for blocking the opening in a sidewall of the housing to minimize fluid leakage from the tip shield upon the arm of the resilient clip moving to the lateral, unbiased position to disengage from the catheter hub.

11. The tip shield of claim 10 wherein the needle holds the arm in the medial, biased position by exerting force along a side of the spring clip thereby pressing the spring clip into the laterally compressed position, and proximal movement of a tip of the needle past the side of the spring clip disengages the arm from the catheter hub by releasing the spring clip into the laterally extended position.

12. The tip shield of claim 11 wherein the means for blocking prevents the arm of the resilient clip from disengaging from the catheter hub until after the distal end of the needle has past the resilient clip.

13. The tip shield of claim 10 wherein the means for blocking is a lid.

14. The tip shield of claim 13 wherein the lid is fabricated from one of plastic, metal, film, high viscosity fluid or a combination thereof.

15. A tip shield for use in a catheter assembly having a needle, a catheter hub, a needle hub, and distal and proximal ends, the tip shield comprising:
a housing having a distal end connectable to the catheter hub and a proximal end connectable to the needle hub;
a compartment within the housing and having an opening through a sidewall of the housing;
a resilient clip insertable through the opening in the sidewall into the compartment, the resilient clip having a U-shaped spring clip, a tab attached to a first end of the U-shaped spring clip, and an arm extending distally from a second end of the U-shaped spring clip, the arm having a finger for engagement with the catheter hub, the spring clip movable toward the tab into a laterally compressed position where the finger is engaged with the catheter hub and the spring clip movable away from the tab into a laterally extended position where the finger is released from the catheter hub; and
a covering extending across the opening in the sidewall of the compartment, the covering being attached to the housing along or near at least one edge of the opening, the covering minimizing leakage of blood out of the opening and minimizing risk of premature release of the resilient clip from the catheter hub.

16. The tip shield of claim 15 wherein the covering is attached to the housing by one of chemical attachment, mechanical attachment and a combination thereof.

17. The tip shield of claim 15 wherein a position of the covering minimizes movement of the resilient clip out of the compartment.

18. The tip shield of claim 15 wherein the tip shield further comprises a post and the covering further comprises a knob which mates with the post.

19. The tip shield of claim 15 wherein the covering is an extension of the housing.

20. The tip shield of claim 15 wherein the covering is an extension of the resilient clip.

* * * * *